(12) United States Patent
Vrancken Peeters

(10) Patent No.: US 11,375,997 B2
(45) Date of Patent: Jul. 5, 2022

(54) SURGICAL SUTURE APPARATUS, COUPLING UNIT, AND METHOD TO PROVIDE A SURGICAL SUTURE APPARATUS

(71) Applicant: Mellon Medical B.V., Nijmegen (NL)

(72) Inventor: Mark-Paul Franciscus Maria Vrancken Peeters, Nijmegen (NL)

(73) Assignee: Mellon Medical B.V., Nijmegen (NL)

( * ) Notice: Subject to any disclaimer, the term of this patent is extended or adjusted under 35 U.S.C. 154(b) by 301 days.

(21) Appl. No.: 15/738,185

(22) PCT Filed: Jul. 7, 2016

(86) PCT No.: PCT/NL2016/050491
§ 371 (c)(1),
(2) Date: Dec. 20, 2017

(87) PCT Pub. No.: WO2017/007316
PCT Pub. Date: Jan. 12, 2017

(65) Prior Publication Data
US 2018/0185023 A1  Jul. 5, 2018

(30) Foreign Application Priority Data

Jul. 7, 2015 (NL) ...................................... 2015110

(51) Int. Cl.
| | | |
|---|---|---|
| *A61B 17/062* | (2006.01) | |
| *A61B 17/04* | (2006.01) | |
| *A61B 17/06* | (2006.01) | |
| A61B 17/00 | (2006.01) | |
| A61B 17/30 | (2006.01) | |

(52) U.S. Cl.
CPC ........ *A61B 17/062* (2013.01); *A61B 17/0482* (2013.01); *A61B 17/0625* (2013.01);
(Continued)

(58) Field of Classification Search
CPC .............. A61B 17/0469; A61B 17/062; A61B 17/0625; A61B 17/29; A61B 17/0482;
(Continued)

(56) References Cited

U.S. PATENT DOCUMENTS

| | | | |
|---|---|---|---|
| 2,601,564 A | * | 6/1952 | Smith ................ A61B 17/0469 606/144 |
| 4,602,631 A | * | 7/1986 | Funatsu ................. A61B 17/12 606/142 |

(Continued)

FOREIGN PATENT DOCUMENTS

WO    2013/032329 A1    3/2013

*Primary Examiner* — Wade Miles
*Assistant Examiner* — Mohammed S Adam
(74) *Attorney, Agent, or Firm* — Hoffmann & Baron, LLP

(57) ABSTRACT

A surgical suture apparatus for passing a double-ended surgical needle forwards and backwards includes a main body, a first jaw element and a second jaw element, each including a holding device to hold a needle-end of the surgical needle. The first jaw element and second jaw element are movable with respect to each other between a take-over position, where a surgical needle can be passed between the first holding device and the second holding device, and an open position. The surgical apparatus further includes an operating device to operate the first holding device and the second holding device to alternately hold the first needle-end by the first holding device and the second needle-end by the second holding device, where the first jaw element is detachably mounted on the main body.

10 Claims, 7 Drawing Sheets

(52) U.S. Cl.
CPC ............. *A61B 2017/0046* (2013.01); *A61B 2017/00398* (2013.01); *A61B 2017/00473* (2013.01); *A61B 2017/0609* (2013.01); *A61B 2017/06057* (2013.01); *A61B 2017/305* (2013.01)

(58) Field of Classification Search
CPC .... A61B 2017/2903; A61B 2017/2906; A61B 2017/2929; A61B 2017/00349; A61B 17/0491; A61B 17/06114
See application file for complete search history.

(56) References Cited

U.S. PATENT DOCUMENTS

| | | | | |
|---|---|---|---|---|
| 5,234,443 | A | * | 8/1993 | Phan ................. A61B 17/0469 606/144 |
| 5,735,862 | A | | 4/1998 | Jennings et al. |
| 5,897,563 | A | * | 4/1999 | Yoon ................... A61B 17/062 606/144 |
| 5,954,731 | A | * | 9/1999 | Yoon ................... A61B 17/062 606/139 |
| 9,427,226 | B2 | * | 8/2016 | Martin ............... A61B 17/0469 |
| 2010/0185218 | A1 | | 7/2010 | Laby et al. |
| 2011/0130773 | A1 | * | 6/2011 | Saliman ............ A61B 17/0469 606/145 |
| 2012/0150199 | A1 | * | 6/2012 | Woodard, Jr ...... A61B 17/0469 606/147 |
| 2014/0257345 | A1 | | 9/2014 | Holwerda |
| 2015/0127025 | A1 | * | 5/2015 | Hamilton ........... A61B 17/0491 606/147 |
| 2016/0030036 | A1 | * | 2/2016 | Belman ............. A61B 17/0625 606/147 |

\* cited by examiner

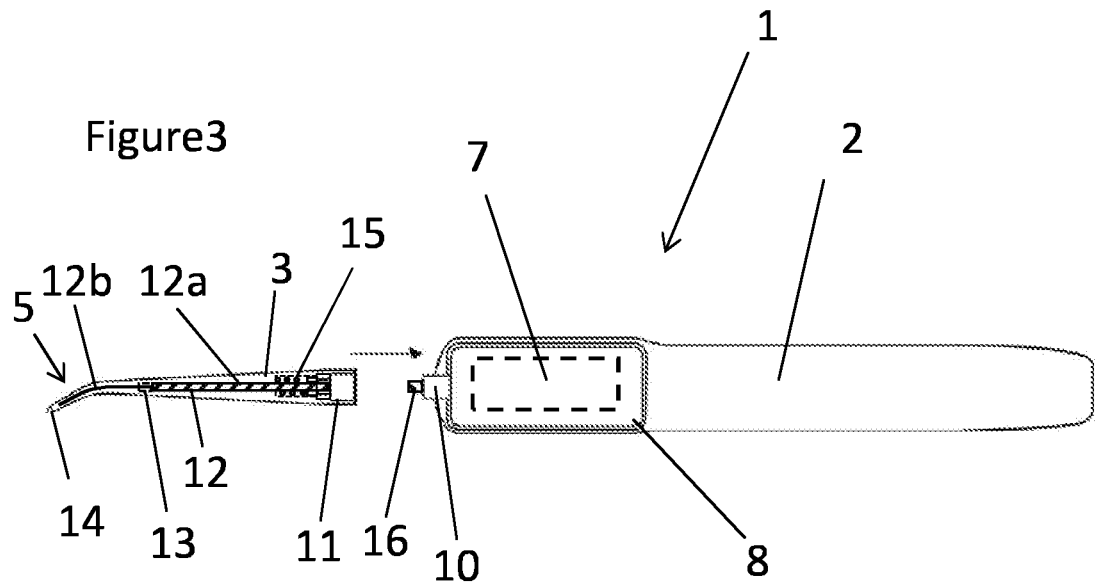
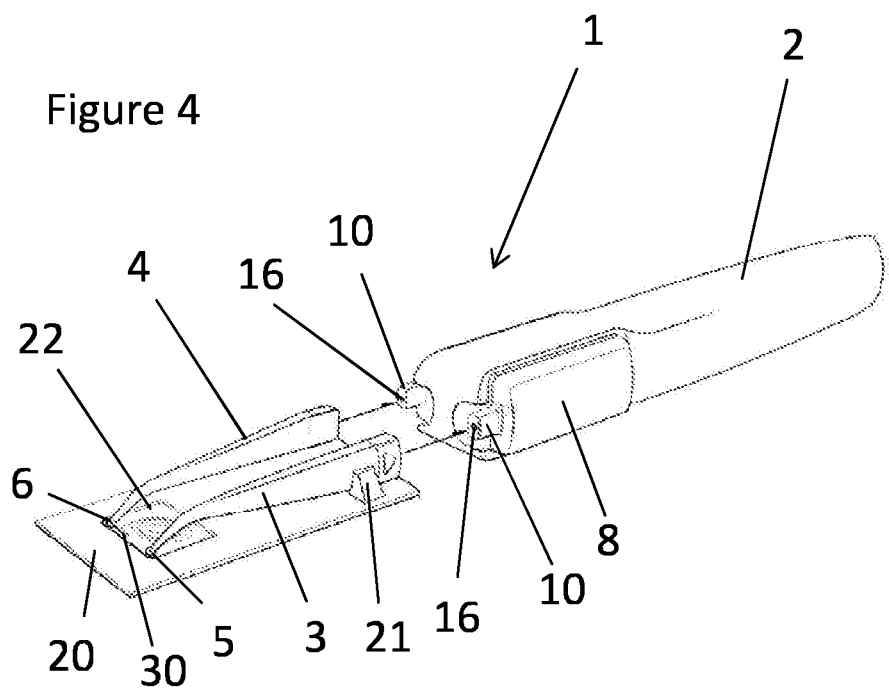

SURGICAL SUTURE APPARATUS, COUPLING UNIT, AND METHOD TO PROVIDE A SURGICAL SUTURE APPARATUS

CROSS-REFERENCE TO RELATED APPLICATIONS

This application is the National Stage of International Application No. PCT/NL2016/050491 filed Jul. 7, 2016, which claims the benefit of Netherlands Application No. NL 2015110, filed Jul. 7, 2015, the contents of which is incorporated by reference herein.

FIELD OF THE INVENTION

The present invention relates to a surgical apparatus, a coupling unit and a method to provide a surgical suture apparatus.

BACKGROUND OF THE INVENTION

WO 2013/032329A1 discloses a surgical suture apparatus configured to pass a double-ended surgical needle backwards and forwards from a first jaw element and a second jaw element. The surgical apparatus comprises a first jaw element and a second jaw element, wherein the first jaw element comprises a first holding device to hold a first needle-end of the surgical needle, and the second jaw element comprises a second holding device to hold a second needle-end of the surgical needle.

The first jaw element and second jaw element are movable with respect to each other between a take-over position wherein a surgical needle can be passed between the first holding device and the second holding device and an open position, wherein the first holding device and the second holding device are spaced further from each other.

The surgical apparatus comprises an operating device to operate the first holding device and the second holding device to alternately hold the first needle-end by the first holding device and the second needle-end by the second holding device.

By actuation of the operating device in the take-over position of the first and second jaw element, the needle can be passed from the first to the second jaw element, or vice versa.

SUMMARY OF THE INVENTION

It is an aim of the present invention to provide an improved surgical apparatus.

The present invention provides a surgical apparatus.

In accordance to the invention, the first jaw element is, at least partly, detachably mounted on the main body of the apparatus.

Such detachable jaw element provides a number of advantages.

For example, a detachable jaw element provides the possibility to mount jaw elements of different sizes and/or shapes on the main body of the surgical apparatus to make the surgical apparatus suitable for different applications. These different sizes and/or shapes may accommodate for longer or shorter needles or needles with different diameters, for a longer or shorter reach of the jaw elements, or jaw elements of different geometry, and/or for a larger or smaller space between the first and second jaw elements, when the first and second jaw elements are in the open position.

Another advantage of a detachable jaw element is that the needle can be held by the holding device of the jaw element before the jaw element is mounted on the main body. In particular, the jaw element and needle-suture combination may be provided as a combination that can be mounted on the main body by a single coupling action between the jaw element and the main body. This takes away the need of separately attaching the needle-suture combination to the jaw element of the surgical apparatus before use.

It is remarked that the jaw element may be completely detachable from the main body, but it is also possible that a part of the jaw element is detachable from the main body. In this application, a detachable jaw element may also refer to a detachable part of the jaw element.

In an embodiment, the surgical apparatus comprises a first coupling device configured to detachably couple the detachable first jaw element or the detachable part thereof to the main body. To obtain a proper connection between the detachable first jaw element and the main body, a coupling device may be provided. The coupling device is configured to couple the detachable jaw element or detachable jaw element part and the main body with each other, which can be established in any suitable way.

In an embodiment, the coupling device comprises a coupling extension mounted on the main body and a coupling recess in the detachable first jaw element, or wherein the coupling device comprises a coupling extension mounted on the detachable first jaw element and a coupling recess in the main body, and wherein the coupling recess is configured to receive the coupling extension in a coupling engagement.

Preferably, the detachable jaw element can be coupled to the main body by a single movement.

A detachable snap-fit connection may be provided to provide a connection between the first jaw element and the main body. Any other way of connecting the jaw element and the main body to each other may also be used.

In an embodiment, the main body comprises the operating device. To take over the needle from the first jaw element to the second jaw element, or vice versa, the operating device is operated in the take-over position of the first and second jaw element such that one of the first and second holding devices releases one needle-end while the other of the first and second holding devices starts to hold the other needle-end.

Since the first holding device is arranged in the detachable first jaw element, the coupling between the first jaw element and the main body may comprise a transfer device configured to transfer an actuation movement of the operating device to the first holding device.

For example, the first holding device and the second holding device may each comprise an elongate needle holding element that can be moved between a holding position in which the needle holding element extends into a needle recess, and a free position in which the needle holding element does not extend into the needle recess. The needle recess may be provided in the first and second jaw element to receive a needle-end of the needle. The needle may be provided with a groove into which the needle holding element may be placed when the needle holding element is arranged in the holding position.

In such embodiment, the transfer device may for example comprise a pusher element that is capable of, dependent upon the state of the operating device, moving/holding the needle holding element to/in the holding position. A biasing element, such as a spring element, may be provided in the detachable jaw element to move/hold the needle to/in the free position. The transfer device may also comprise a connector element configured to be coupled to the holding element to move the holding element both from the free position to the holding position and from the holding position to the free position. Any other suitable transfer device may also be used.

In an embodiment, the first jaw element comprises a detachable jaw element part and a non-detachable jaw element part, wherein the detachable jaw element part is detachably mounted on the non-detachable jaw element part. In this embodiment only a part of the first jaw element is detachable from the main body, while the non-detachable jaw element part is fixedly connected to the main body of the surgical apparatus. Operating organs, such as operating buttons may typically be provided on the non-detachable jaw element part.

In an embodiment, the second jaw element is, at least partly, detachably mounted on the main body. In this embodiment, both the first and second jaw element may be detachably mounted on the main body of the surgical apparatus.

The second jaw element may have the same features and/or characteristics as described with respect to the first jaw element.

In an embodiment, the surgical apparatus may have, at least with respect to the jaw elements, a symmetric construction, in which the first jaw element and second jaw element are substantially constructed the same, symmetrically with respect to a longitudinal mid-plane of the surgical apparatus.

In an embodiment, the operating device comprises an operating switch to provide, upon activation of the operating switch, a switch signal, and one or more actuators configured to be controlled by the switch signal to operate the first holding device and the second holding device, wherein the operating switch and the one or more actuators are provided in the main body.

Thus, operation of the first holding device and the second holding device is carried out on the basis of a switch signal provided by the operating switch. The operating switch may be a separate device or may be incorporated in a control device, such as a processor configured to provide a switch signal on the basis of input signals, for example the positions of the first and second jaw elements measured by position sensors.

The switch signal is preferably an electrical switch signal, but may also be a signal of another type, such as a magnetic signal, a pneumatic signal, a hydraulic signal or a thermal signal.

The one or more actuators may be of any type of actuator suitable to operate the first holding device and/or the second holding device. This may for example be pneumatic, thermal or piezoelectric actuators. Preferably the one or more actuators are electrical motors.

An important advantage of using a switch signal, in particular an electrical switch signal is that the design of the first jaw element and the second jaw element is less dependent on the movements of a mechanical system arranged between an operating button and the first holding device and the second holding device. Therefore, the movements of the first jaw element and the second jaw element may be designed with more freedom.

This movement is preferably designed as the movement of two jaws of a pair of tweezers, but may also be any other suitable movement. The surgical needle may for example be a straight needle.

It is remarked that, in alternative embodiments, the operating device comprising an operating switch and/or the one or more actuators configured to be controlled by the switch signal to operate the first holding device and the second holding device, may also be, at least partially, arranged in the first and/or second jaw element.

In an embodiment, the operating switch is configured to be automatically activated when the first and the second jaw element are moved into the take-over position. In such embodiment, the operating switch will be operated in dependence of the position of the first and second jaw element. As soon as the first and second jaw elements are positioned in the take-over position, the operating switch will be activated and the one or more actuators will be actuated such that the needle is taken over between the first holding device and the second holding device.

In such embodiment, the operating device may comprise a first contact element arranged on the first jaw element and a second contact element, wherein the first contact element and second contact element come into contact with each other, when the first jaw element and the second jaw element are moved into the take-over position. The second contact element may be arranged on the second jaw element.

In an embodiment, the surgical apparatus comprises an operating organ configured to operate the operating switch. In such embodiment a separate actuation of the operating organ, for example an operating button, is required to establish the activation of the operating switch to control the one or more actuators to operate the first holding device and the second holding device.

It is remarked that the automatic activation, as soon as the first jaw element and the second jaw element are moved into the take-over position, may also be provided in combination with an operating organ configured to operate the operating switch.

When in such embodiment, the first jaw element and the second jaw element are moved into the take-over position, the operating switch will be automatically activated to operate the first and second holding device. As a result, the needle is taken over from the first holding device to the second holding device, or vice versa. It may however occur that the physician carrying out the surgical procedure determines that the needle has been passed through the human or animal tissue at a sub-optimal location. Since the needle already has been passed to the other holding device, the needle cannot directly be pulled out of the tissue at the side where it has been introduced into the tissue.

By actuation of the operating organ, the needle can, when the first and second jaw element are still in the take-over position, again be taken over by the first holding device, and the needle can be pulled out of the tissue at the side where it has been pierced into the tissue.

In an embodiment, the surgical apparatus comprises a sensor device configured to determine whether the first jaw element and the second jaw element are positioned in the take-over position. The sensor device may for example comprise a first contact element and a second contact element that are arranged in the surgical apparatus such that the first contact element and the second contact element will only come into contact with each other when the first and second jaw elements are arranged in the take-over position. The sensor device may be any device capable of determining that the first and second jaw elements are positioned in the take-over position.

In an embodiment, the operating switch is configured to provide the switch signal only when the sensor device has determined that the first jaw element and the second jaw element are positioned in the take-over position, or wherein the one or more actuators are configured to operate the first holding device and the second holding device only when the sensor device has determined that the first jaw element and the second jaw element are positioned in the take-over position. In this embodiment, the one or more actuators can only operate the first holding device and the second holding device when the first jaw element and the second jaw element are in the take-over position.

It is ensured that the first holding device and the second holding device are not operated, as long as the first jaw element and the second jaw element are not positioned in the take-over position, by preventing that the operating switch provides the switch signal, or by preventing that the one or more actuators operate the first holding device and the second holding device, even though a switch signal is received.

The sensor device is not limited to a device configured to provide an electrical output signal, but may also for example be a mechanical stop that prevents depression of an operating button as long as the first jaw element and the second jaw element are not positioned in the take-over position.

In an embodiment, the surgical apparatus comprises a first actuator to operate the first holding device and a second actuator to operate the second holding device. By providing a first actuator for the first holding device and a second actuator for the second holding device, a relatively simple and direct actuation of the first holding device and the second holding device may be realized.

The first actuator and the second actuator may for instance be electrically activated motors, such as linear solenoids, stepper motors, Direct Current (DC) motors and servomotors.

In an embodiment, the surgical apparatus comprises a two-position mechanism having a first position in which a needle-end may be held by the first holding device, and a second position in which a needle-end may be held by the second holding device, wherein the one or more actuators are configured to actuate the two-position mechanism. When a two-position switch mechanism is used to actuate the first holding device and the second holding device, a single actuator may be sufficient to operate the two-position switch mechanism.

It is remarked that the operating device comprising an operating switch and one or more actuators configured to be controlled by the switch signal to operate the first holding device and the second holding device, may also be applied in a surgical apparatus in which the first jaw element and/or second jaw element are non-detachably mounted on the main body.

The invention also provides a coupling unit, comprising a holder, and
a first detachable jaw element or a detachable part thereof, comprising a first holding device configured to hold a needle-end of a double-ended surgical needle, wherein the detachable first jaw element or the detachable part thereof is configured to be coupled to a main body of a surgical apparatus,
wherein the holder is configured to releasably hold the detachable first jaw element or the detachable part thereof in a fixed position with respect to the holder.

By providing a coupling unit comprising a first detachable jaw element and a holder holding the first jaw element, the first jaw element can be mounted on the main body without the need of holding the detachable jaw element itself. This may be advantageous as the holder may be designed to conveniently hold and position the first jaw element during coupling of the first jaw element to the main body. Further, a needle-suture combination may already be coupled to the first jaw element, while the holder accommodates this needle-suture combination without the risk of injury due to the needle or damaging the needle, for example by exerting a bending force on the needle.

Further, the holder can be shaped to give proper support during coupling of the jaw element and the main body. After coupling of the jaw element to the main body, the jaw element can be released from the holder.

In an embodiment, the coupling unit further comprises a second detachable jaw element or a detachable part thereof comprising a second holding device configured to hold a needle-end of the double-ended surgical needle, wherein the second detachable jaw element or the detachable part thereof is configured to be coupled to the main body of the surgical apparatus, and wherein the holder is configured to releasably hold the detachable second jaw element or the detachable part thereof in a fixed position with respect to the holder.

The holder can be configured to releasably hold a first jaw element and a second jaw element, whereby the first jaw element and second jaw element are held in such configuration that the first jaw element and the second jaw element can be coupled to the main body of a surgical apparatus by a single movement of the first jaw element and the second jaw element.

In an embodiment, the coupling unit further comprises a needle-suture combination having a double-ended surgical needle, wherein one needle-end of the needle is held by or arranged in the first holding device, and wherein the holder is preferably configured to hold the needle-suture combination.

When the needle-suture combination is already coupled to the first jaw element, only the one or two detachable jaw elements have to be coupled to the main body in order to make the surgical apparatus ready for use. This has the advantage that less time is required to prepare the surgical apparatus, since the needle-suture combination does not have to be separately coupled to the respective jaw element. Furthermore, there is less risk on an incorrect mounting of the needle on the jaw element.

The holder may be designed such that the holder prevents or substantially reduces the risk that a person is pierced by the needle, for example when mounting the needle-suture combination, separately or together with the jaw element, on the surgical apparatus. The holder may for this reason comprise a recess in which the needle can extend, when the needle-suture combination is mounted on the holder. The holder may also comprise an area, for example an enclosed space to accommodate the suture attached to the needle.

The invention also provides a method of providing a surgical suture apparatus having a main body and a first detachable jaw element to be mounted on the main body, comprising the steps of:
providing a main body of the apparatus, and
providing at least one coupling unit,
coupling the first detachable jaw element or the detachable part thereof to the main body while holding the coupling unit in one hand and the main body in another hand, and subsequently releasing the first detachable jaw element or the detachable part thereof from the holder.

In an embodiment, the coupling unit further comprises a second detachable jaw element or a detachable part thereof, comprising a second holding device configured to hold a needle-end of the double-ended surgical needle, wherein the method comprises coupling the second detachable jaw element or the detachable part thereof to the main body while holding the coupling unit in one hand and the main body in another hand.

In an embodiment, coupling of the first detachable jaw element or the detachable part thereof to the main body and coupling of the second detachable jaw element or the detachable part thereof to the main body is carried out simultaneously.

In an embodiment, the method comprises providing multiple coupling units, wherein the multiple coupling units differ from each other in size and/or shape of the first detachable jaw element or the detachable part thereof and/or second detachable jaw element or the detachable part thereof, and wherein the method comprises selecting the coupling unit to be used for coupling the first detachable jaw element or the detachable part thereof and/or the second detachable jaw element or the detachable part thereof to the main body.

In an embodiment, the method comprises providing multiple main bodies, wherein the multiple main bodies differ from each other in size and/or shape, and wherein the method comprises selecting the main body to be used for coupling the first and/or second detachable jaw elements to the main body.

As explained above, an important advantage of at least one detachable jaw element is that the size and/or shape of the detachable jaw elements and/or the size of the main body can be adapted to the desired application. For example, a detachable jaw element provides the possibility to mount jaw elements of different sizes and/or shapes on the main body of the surgical apparatus to make the surgical apparatus suitable for different applications. Also, different surgical procedures may be performed more accurately or efficiently when main bodies of different shapes or sizes can be used.

The step of selecting the jaw elements and/or main body to be used in a certain application may therefore be an important step in providing a surgical suture apparatus for a specific application.

BRIEF DESCRIPTION OF THE DRAWINGS

Further characteristics and features of embodiments of the invention will be described hereinafter, whereby reference will be made to the accompanying drawings, in which:

FIG. 3 shows the cross section of FIG. 2 before coupling of the jaw elements to the main body;

FIG. 4 shows a perspective view of the main body of the surgical apparatus of FIG. 1 and a coupling unit comprising two jaw elements;

DETAILED DESCRIPTION OF THE INVENTION

Figure 1:
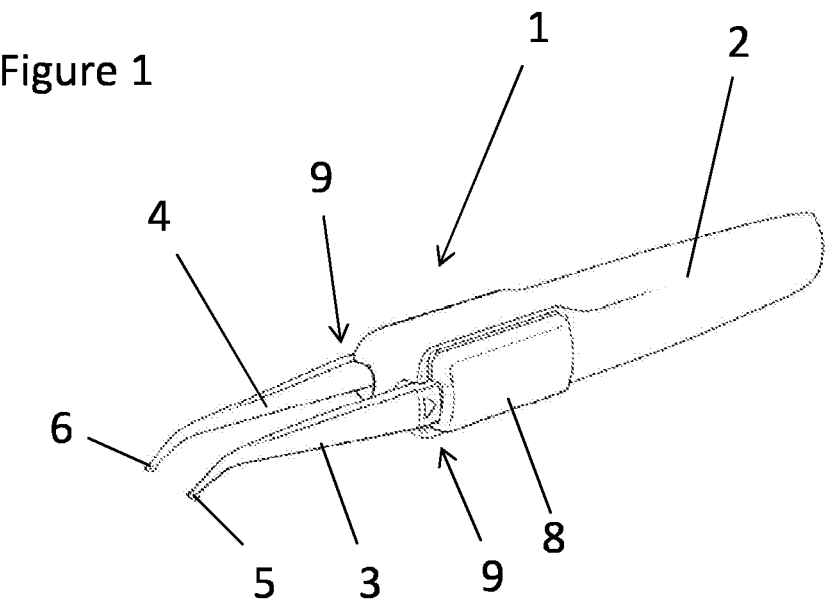
FIG. 1 shows a perspective view of an embodiment of a surgical apparatus according to the invention.

FIG. 1 shows schematically an embodiment of a surgical apparatus of the invention. The surgical apparatus is generally indicated by reference numeral 1.

The surgical apparatus 1 comprises a main body 2 and a first detachable jaw element 3 and a second detachable jaw element 4. The first jaw element 3 comprises a first holding device 5 configured to hold a needle-end and the second jaw element 4 comprises a second holding device 6 also configured to hold a needle-end. The first jaw element 3 and the second jaw element 4 are detachably mounted on the main body 2.

The surgical apparatus 1 is configured to pass a double-ended surgical needle forwards and backwards so that the surgical apparatus can be used to apply sutures to a human or animal body. The main body 2, and the detachable jaw elements 3 and 4 may be made of any suitable material such as a (non-toxic and/or biocompatible) plastics or metal.

The first jaw element 3 and the second jaw element 4 are movable with respect to each other between a take-over position, wherein a surgical needle can be taken over between the first holding device 5 and the second holding device 6 and an open position, wherein the first holding device 5 and the second holding device 6 are spaced further from each other. In FIG. 1, the surgical apparatus 1 is shown in the open position. In this open position body tissue can be placed between the first jaw element 3 and the second jaw element 4.

In the main body 2 an operating device 7 is provided to operate the first holding device 5 and the second holding device 6, to alternately hold the first needle-end by the first holding device 5 and the second needle-end by the second holding device 6. When the first jaw element 3 and the second jaw element 4 are held in the take-over position, actuation of the operating device 7 will result in that a needle held by the first holding device 5 will be taken over (through the human or animal tissue) by the second holding device 6, since operating the operating device 7 will cause the second holding device 6 to hold one needle-end, while the first holding device 5 will release the other end of the needle.

Operating buttons 8 are provided to move the first jaw element 3 and the second jaw element 4 with respect to each other from the open position to the take-over position. Actuation of the operating device 7 can for instance be established by further depression of one or more operating buttons 8 and/or by depression of a separate operating button.

Figure 2:
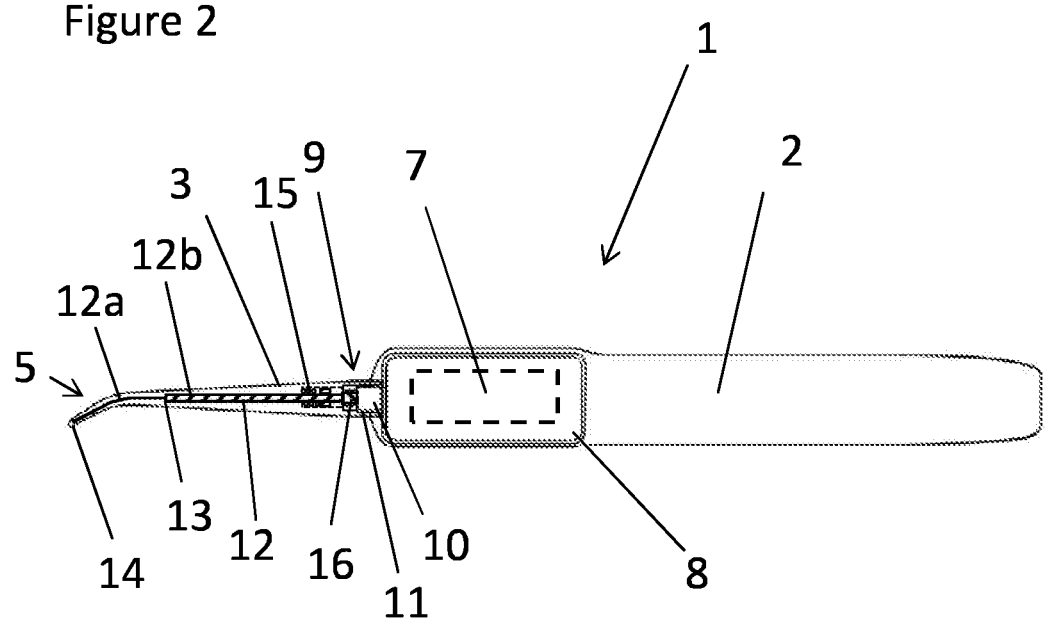
FIG. 2 shows a cross section of the embodiment of FIG. 1.

FIG. 2 shows a cross section of the embodiment of FIG. 1, wherein the first jaw element 3 and the second jaw element 4 are mounted on the main body 2. A coupling device 9 is provided to detachably couple the first jaw element 3 on the main body 1. A similar coupling device (not shown) is provided to couple the second jaw element 4 on the main body 1.

The coupling device 9 comprises a coupling extension 10 on the main body 2 and a coupling recess 11 in the first jaw element 3. The coupling extension 10 and the coupling recess 11 are shaped to provide a snap-fit connection between the first jaw element 3 and the main body 2. For example, the coupling extension 10 and/or the coupling recess 11 may have rims that cooperate to create the snap-fit connection. However, any other connection to couple the main body 2 and the first jaw element 3 may also be used.

Since the operating device 7 is arranged in the main body 2, the operating movements of the operating device 7 have to be transferred to the first holding device 5 and the second holding device 6 in the first detachable jaw element 3 and the second detachable jaw element 4, respectively, in order to carry out a take-over of the needle between the first holding device 5 and the second holding device 6.

The first holding device 5 comprises an elongate holding element 12 comprising a rigid holding element part 12a and a flexible holding element part 12b. The holding element 12 is arranged in a guiding channel 13 provided in the first detachable jaw element 3. In this guiding channel 13 the holding element 12 can be moved in longitudinal direction of the first jaw element 3 between a holding position (FIG. 2) and a free position (FIG. 3).

During this longitudinal movement of the holding element 12 through the guiding channel 13, the flexible holding element part 12b may adapt its shape to the form of the guiding channel 13.

In the holding position, a needle arranged in a needle recess 14 of the first holding device 5 will be held by a distal end of the flexible holding element part 12b, for example by extending into a radial or tangential opening, such as a groove, provided in the needle. The presence of the distal end of the flexible holding element part 12b in the groove prevents that the needle can be pulled out of the needle recess 14.

In the free position, the holding element 12, in particular the distal end of the second holding element part 12b will not extend into the groove, typically by retracting the holding element 12 out of the needle recess 14, so that the needle is free to move, in its longitudinal direction, into and out of the needle recess 14 of the first holding device 5.

A spring element 15 is provided to bias the holding element 12 to the free position.

The operating device 7 comprises a pusher element 16 which is movable between a retracted position and an extended position. By movement of the pusher element 16 from the retracted position to the extended position, the holding element 12 may be pushed by the pusher element 16, against the biasing force of spring element 15, from the free position to the holding position. When the pusher element 16 is held in the extended position the holding element 12 will be in the holding position to hold a needle end of a needle placed in the needle recess 14.

Correspondingly, the operating device 7 comprises a pusher element 16 in the coupling extension 10 of the coupling device 9 for the second jaw element 4. This pusher element 16 is configured to move the holding element 12 in the second jaw element 4, against the biasing force of spring element 15, from the free position to the holding position The operating device 7 is configured to always position one of the pusher elements 16 in the extended position so that the needle will always be held by at least one of the first holding device 5 and the second holding device 6.

FIG. 3 shows the surgical apparatus 1 of FIGS. 1 and 2, but before coupling of the first jaw element 3 and the second jaw element 4 on the main body 2. In FIG. 3, the movement of the first jaw element 3 with respect to the main body 2 in order to fix the first jaw element 3 on the main body 2 is indicated by an arrow. The first jaw element 3 and the second jaw element 4 can be separately coupled to the main body 2. Since no pressure is exerted by a pusher element 16 on the holding element 12, the spring element 15 biases the holding element 12 to the free position.

FIG. 4 shows an embodiment in which the first jaw element 3 and the second jaw element 4 are provided on a holder 20. The holder 20 comprises gripping elements 21 to hold the first jaw element 3 and the second jaw element 4 in a fixed relationship. The use of this holder 20 has the advantage that the first jaw element 3 and the second jaw element 4 can be simultaneously coupled to the main body 2 by a single linear movement of the holder with respect to the main body 2, as indicated by arrows in FIG. 4.

Furthermore, the holder 20 can due to its shape and size more easily be manipulated than the separate jaw elements, which further improves the ease of use.

The holder 20 also holds a needle-suture combination 30 comprising a double-ended needle and a suture attached to the needle. One needle-end is arranged in the second holding device 6 of the second jaw element 4. A recess 22 is provided to define a space in which the needle-suture combination is received.

By coupling of the first jaw element 3 and the second jaw element 4 by a single movement of the holder 20 with respect to the main body 2, not only couples the first jaw element 3 and the second jaw element 4 to the main body 2, but also directly attaches a needle-suture combination 30 to the surgical apparatus. After coupling of the first jaw element 3 and the second jaw element 4 to the main body 2, the holder 20 can be released from the first jaw element 3, the second jaw element 4, and the needle-suture combination 30, and the surgical apparatus 1 is ready for use.

By providing the needle-suture combination on the holder 20, while being held by the first holding device 5 or second holding device 6, the surgical apparatus 1 is directly ready for use after coupling of the first detachable jaw element 3 and the second detachable jaw element 4. Furthermore, the risk that a user is injured by the needle may be substantially reduced by providing the needle-suture combination 30 on the holder 20.

Figure 5:
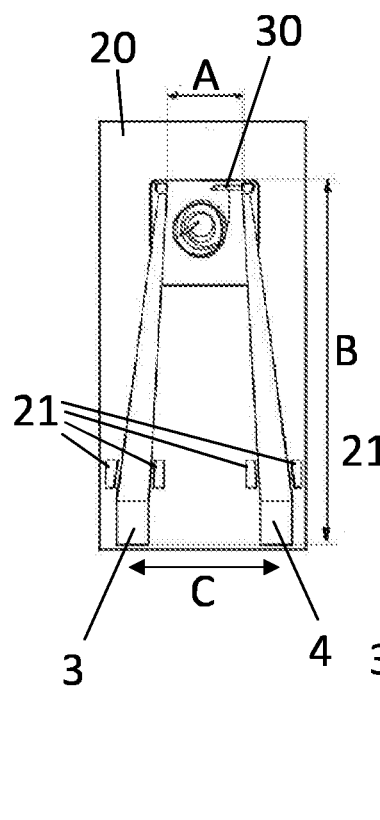
FIGS. 5, 6 and 7 show different embodiments of a coupling unit according to the invention.
Figure 6:
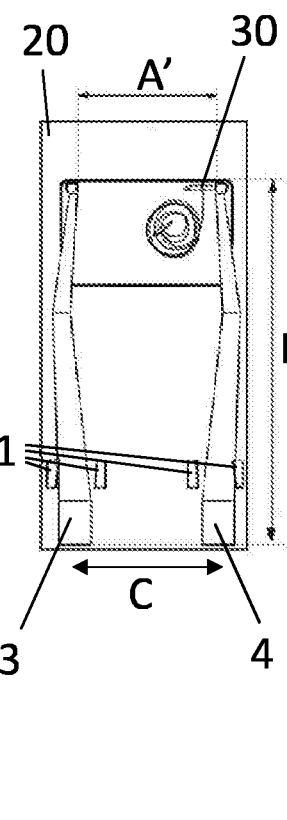
Figure 7:
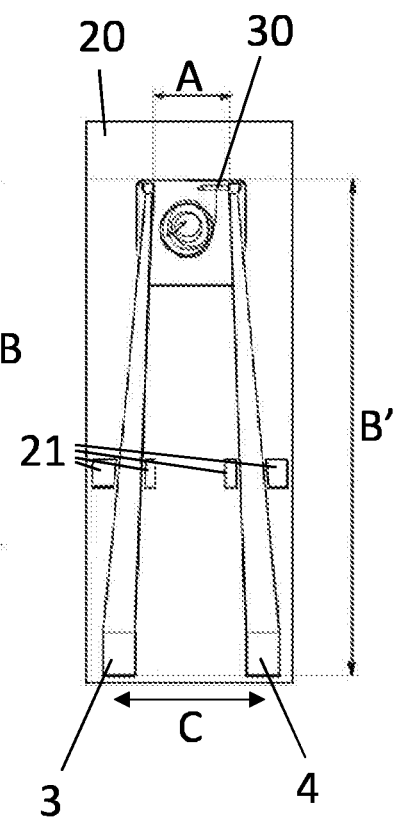

FIGS. 5, 6 and 7 show three different embodiments of a coupling unit comprising a holder 20, a first jaw element 3, a second jaw element 4 and a needle-suture combination 30. The first jaw element 3 and the second jaw element 4 each comprise a proximal end to be coupled to the main body 2 and a distal end to hold a needle-end of the needle-suture combination 30.

In all embodiments of FIGS. 5, 6 and 7, the distance C between the proximal ends of the first jaw element 3 and the second jaw element 4 is the same. This ensures that the first jaw element 3 and the second jaw element 4 can be coupled to the main body 2 by a single movement of the holder 20 with respect to the main body 2. The distance C corresponds with the distance between the coupling extensions 10 of the main body 2, as the main body 2 is normally biased to hold the first jaw element 3 and the second jaw element 4 in the open position, when the first jaw element 3 and the second jaw element 4 are coupled to the main body 2.

FIG. 5 shows a first embodiment, in which the detachable first jaw element 3 and second jaw element 4 each have a length B and a distance A between the distal ends of the first jaw element 3 and the second jaw element 4.

FIG. 6 shows a coupling unit having jaw elements 3 and 4 of the same length B as shown in FIG. 5, but with a larger distance A' between the distal ends of the first jaw element 3 and the second jaw element 4. This larger distance A' and the shape of the first jaw element 3 and the second jaw element 4 provide a larger space between the jaw elements 3 and 4, which may be advantageous in certain applications of the surgical apparatus 1. The larger distance A' between the distal ends of the first jaw element 3 and the second jaw element 4, can also be used to provide a longer needle in the needle-suture combination 30.

FIG. 7 shows another embodiment of a coupling unit. The jaw elements 3 and 4 of this embodiment have the same distance A between the distal ends of the first jaw element 3 and the second jaw element 4 as shown in FIG. 5, but the length B' of the first jaw element 3 and the second jaw element 4 is substantially larger than in the embodiment of FIG. 5. This larger length B' provides a longer reach with the surgical apparatus 1, which also may be advantageous in certain surgical applications.

It will be clear to the man skilled in the art of suturing, that other variations may be provided to meet requirements or needs for specific applications of the surgical apparatus.

Further, it is remarked that in an embodiment of the invention different types of main bodies, for example having different shapes or sizes, may be provided. Dependent on the application the most suitable main body may be selected to from a surgical apparatus.

Figure 8:
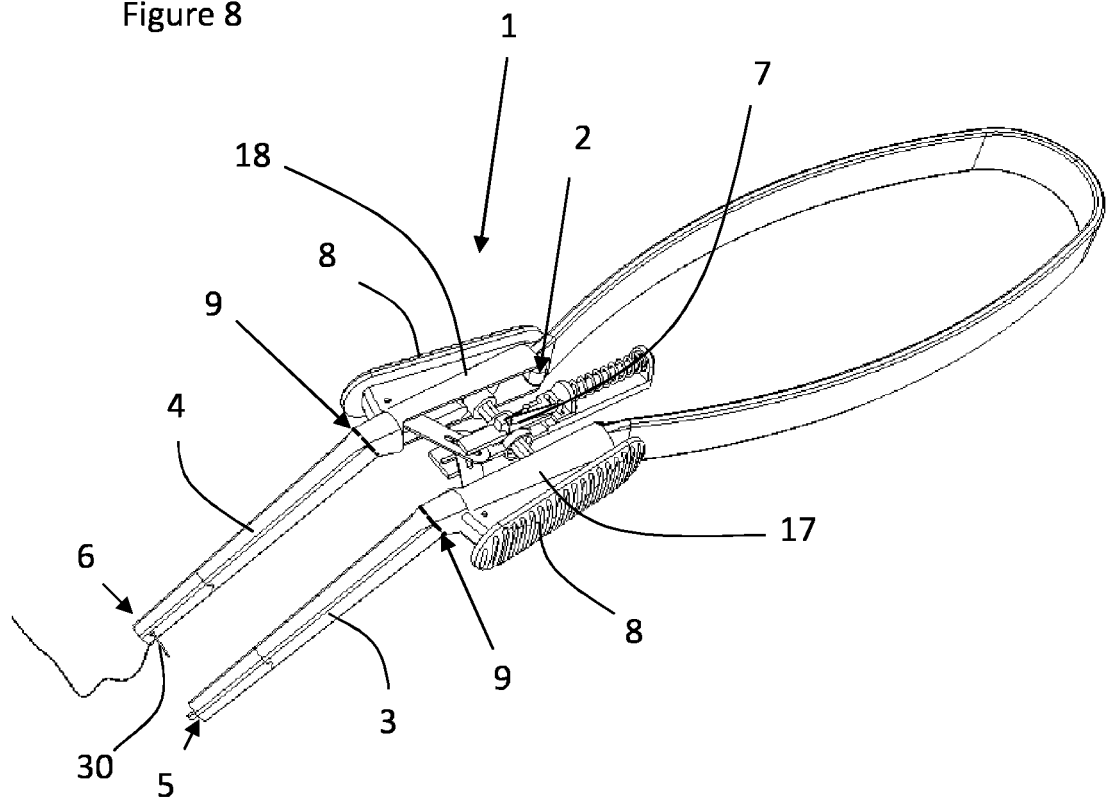
FIGS. 8 and 9 show a perspective view of an alternative embodiment of the invention.
Figure 9:
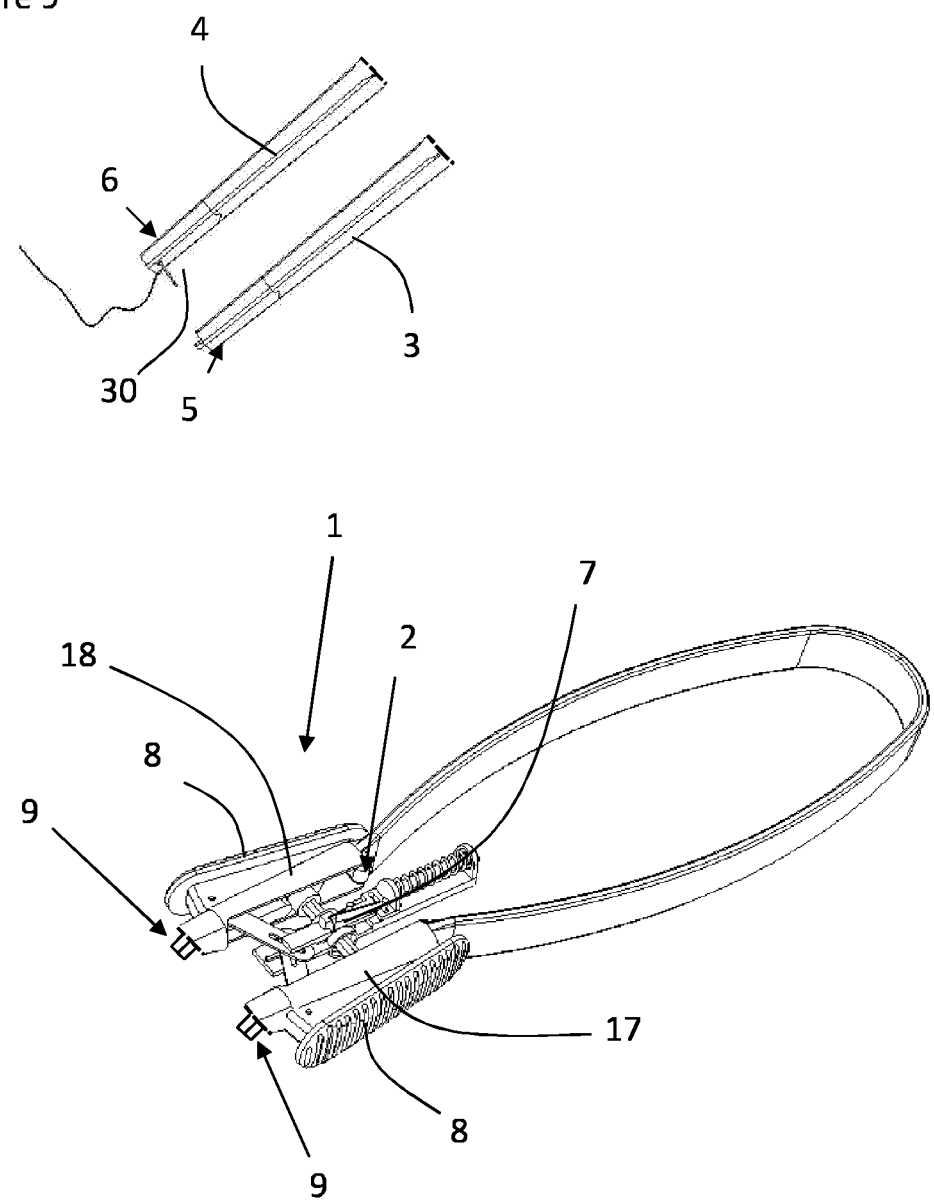

FIGS. 8 and 9 show an alternative embodiment of a surgical apparatus according to the invention. The surgical apparatus of FIG. 8 comprises a main body 2, a first jaw element 3 and a second jaw element 4. The main body 2 comprises an operating device 7 and operating buttons 8.

The construction of the surgical apparatus of FIGS. 8 and 9 is similar to the surgical apparatus disclosed in WO 2013/032329A. The main difference is the construction of the jaw elements. The first jaw element and the second jaw element of the surgical apparatus of WO 2013/032329A are completely permanently fixed to the main body of the surgical apparatus. It is not possible to detach, completely or partly, the jaw elements of the apparatus of WO 2013/032329A.

In contrast, the jaw elements of the surgical apparatus of FIGS. 8 and 9 comprise a first detachable jaw element part 3 and a second detachable jaw element part 4 detachably mounted on the main body 2 with coupling devices 9. As a result, the first detachable jaw element part 3 and/or the second detachable jaw element part 4 can be detached from the main body 2 and for example exchanged for another set of a first jaw element 3 and a second jaw element 4.

In FIG. 8, the first detachable jaw element part 3 and the second detachable jaw element part 4 are coupled to the main body 2, while in FIG. 9, the main body 2, the first detachable jaw element part 3 and the second detachable jaw element part 4 are shown separately, i.e. before coupling of the first detachable jaw element part 3 and the second detachable jaw element part 4 to the main body 2.

In the coupled state, the first detachable jaw element part 3 is coupled to a first non-detachable jaw element part 17 and the second detachable jaw element part 4 is coupled to a second non-detachable jaw element part 18. Thus, the first non-detachable jaw element part 17 and the second non-detachable jaw element part 18 are parts of the main body 2.

When during use a pinching force is exerted on the operating buttons 8, the first non-detachable jaw element part 17 will move towards the second non-detachable jaw element part 18 and, as a result, the first detachable jaw element part 3 will move towards the second detachable jaw element part 4, until the first detachable jaw element part 3 and the second detachable jaw element part 4 are positioned in the take-over position. In this position, the transfer of the needle-suture combination 30 from one holding device 5 or 6 to the other holding device 6 or 5 can be effectuated by activation of the operating device 7.

Figure 10:
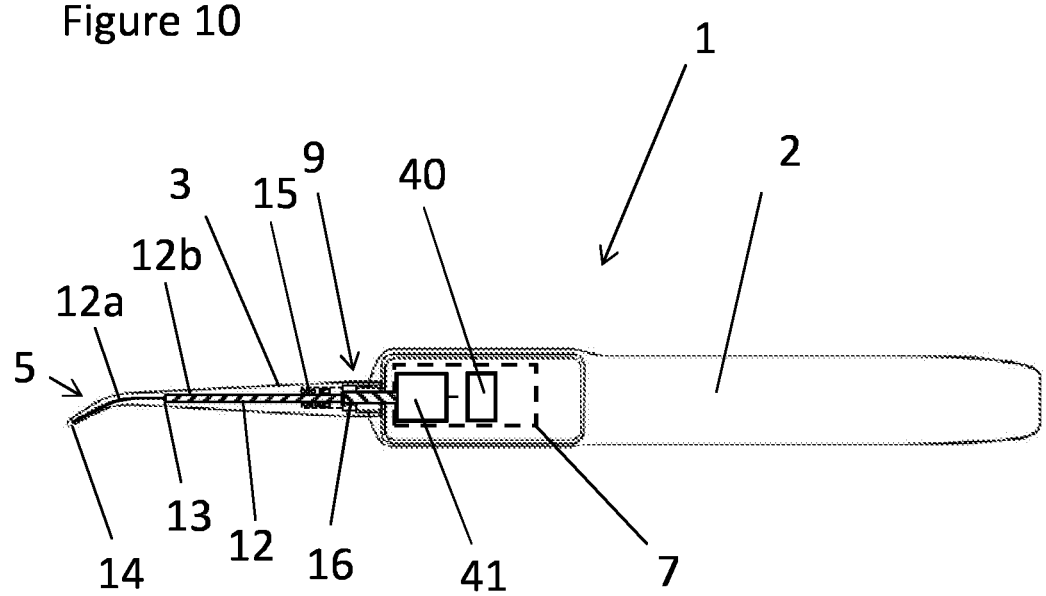
FIGS. 10 and 11 show the embodiment of FIG. 1 showing an exemplary embodiment of the operating device in more detail.
Figure 11:
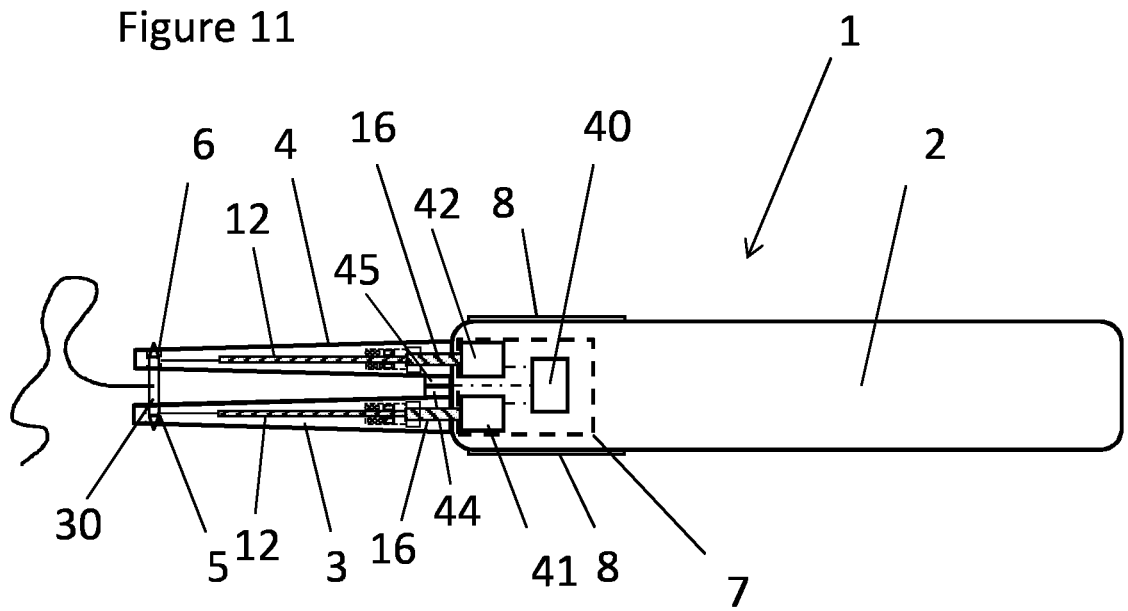

FIGS. 10 and 11 show an embodiment of the operating device 7 of the surgical apparatus in FIG. 1 in more detail. The operating device 7 comprises an operating switch 40 to provide, upon activation of the operating switch 40, an electrical switch signal, and a first actuator 41 configured to operate the first holding device 5, and a second actuator 42 configured to operate the second holding device 6. The operating switch 40, the first actuator 41 and the second actuator 42 are arranged in the main body 2 of the surgical apparatus 1.

The first actuator 41 is connected to the pusher element 16 in order to displace the pusher element 16 between an extended position and a retracted position to move the holding element 12 of the first holding device 5 between the holding position and the free position.

Correspondingly, the second actuator 42 is connected to the pusher element 16 in order to displace the pusher element 16 between an extended position and a retracted position to move the holding element 12 of the second holding device 6 between the holding position and the free position.

The first actuator 41 and the second actuator 42 are linear actuators, such as solenoids, that can be controlled by an electrical operating switch signal provided by the operating switch 40. Also, other motor types can be used such as stepper motors, DC motors and servomotors, whereby, in the case of rotary motors, a rotary movement of the motor is converted into a linear movement of the holding elements 12.

The linear movement of the first actuator 41 and the second actuator 42 is thus used to move the respective holding element 12 into and out of the needle-recess of the respective holding device 5, 6.

The first actuator 41 and the second actuator 42 are controlled by the operating switch 40 in such a way that when a needle is held by one of the first holding device 5 and the second holding device 6, the other of the first holding device 5 and the second holding device 6 is in the free position, and vice versa.

As soon as an electrical operating switch signal is provided by the operating switch 40, the first actuator 41 and the second actuator 42 will be activated to move one holding element 12 from the holding position to the free position, and the other holding element 12 from the free position to the holding position. As a result, the needle-suture combination 30 is taken over from one of the first jaw element 3 and the second jaw element 4 to the other of the first jaw element 3 and the second jaw element 4.

As shown in FIG. 11, the operating device 7 comprises a first contact element 44 mounted on the first jaw element 3 and a second contact element 45 mounted on the second jaw element 4. In the take-over position of the first jaw element 3 and the second jaw element 4, as shown in FIG. 11, the first contact element 44 and the second contact element 45 are in contact with each other, while in an open position, in which the first jaw element 3 and the second jaw element 4 are spaced further from each other, there is no contact between the first jaw element 3 and the second jaw element 4.

When the first contact element 44 and the second contact element 45 are in contact with each other, an electrical circuit will be closed, which electrical circuit runs via the operating switch 40, and therefore the operating switch can determine whether the first jaw element 3 and the second jaw element 4 are in the take-over position or in another position. Thus, the first contact element 44 and the second contact element 45 can be used as a sensor device to determine whether the first jaw element 3 and the second jaw element 4 are in the take-over position.

Any other sensor device configured to determine whether the first jaw element 3 and the second jaw element 4 are in the take-over position may also be used.

The operating switch 40 is configured to be automatically activated when the first jaw element 3 and the second jaw element 4 are moved into the take-over position by depression of the operating buttons 8. This means that as soon as the first contact element 44 and the second contact element 45 come into contact with each other, the electrical circuit will be closed and, as a result, the operating switch 40 will provide automatically an electrical switch signal to the first actuator 41 and the second actuator 42 so that the needle-suture combination 30 will be taken over between the first holding device 5 and the second holding device 6, or vice versa.

Since movement of the first jaw element 3 and the second jaw element 4 into the take-over position results in automatic take-over from the needle-suture combination 30 being held by the first holding device 5 and the second holding device 6, or vice versa, this has the consequence that, when the physician, who is carrying out a surgical procedure, would determine after movement of the first jaw element 3 and the second jaw element into the take-over position, that the needle has been passed through human or animal body tissue at a sub-optimal location, the needle-suture combination 30 is already taken over by the other holding device.

In order to correct the position of the needle of the needle-suture combination 30, the surgical apparatus 1 may be provided with a further operating button (not shown) that enables active operation of the operating switch 40. When the electrical circuit is closed by contact between the first contact element 44 and the second contact element 45, i.e. the first jaw element 3 and the second jaw element 4 are brought in the take-over position, by depression of the operating buttons 15, activation of the further operating button will activate the operating switch 40 to provide an electrical switch signal to the first actuator 41 and the second actuator 42 in order to take over the needle-suture combination 30 between the first holding device 5 and the second holding device 6. The further operating button may be integrated in the operating buttons, for example an additional button or further depression of the operating buttons 15.

Thus, when the physician, who is carrying out a surgical procedure, would determine that the needle-suture combination 30 has been passed through human or animal body tissue at a sub-optimal location, depression of the further operating button would cause the needle-suture combination 30 to be taken over by the holding device that was holding the needle-suture combination 30, before the automatic take-over caused by movement of the first jaw element 3 and the second jaw element 4 into the take-over position. As a consequence, the needle-suture combination 30 can be pulled out of the tissue at the same side as from which it was pierced into the tissue, and the side where the needle-suture combination 30 is retracted from the body tissue can be corrected.

In an alternative embodiment, the operating device 7 may be configured to only take over the needle-suture combination 30 between the first holding device 5 and the second holding device 6, when there is a separate activation of the operating switch 40, i.e. no automatic activation when the first jaw element 3 and the second jaw element 4 are moved into the take-over position. Such separate activation may be initiated by a further operating button or further depression of the operating buttons 15, but also by any other suitable activation device.

In the embodiment of FIGS. 10 and 11, a first actuator 41 and a second actuator 42 are provided wherein the first actuator 41 is provided to actuate a first holding element 12 of the first holding device 5, and the second actuator 42 is provided to actuate a second holding element 12 of the second holding device 6.

Figure 12:
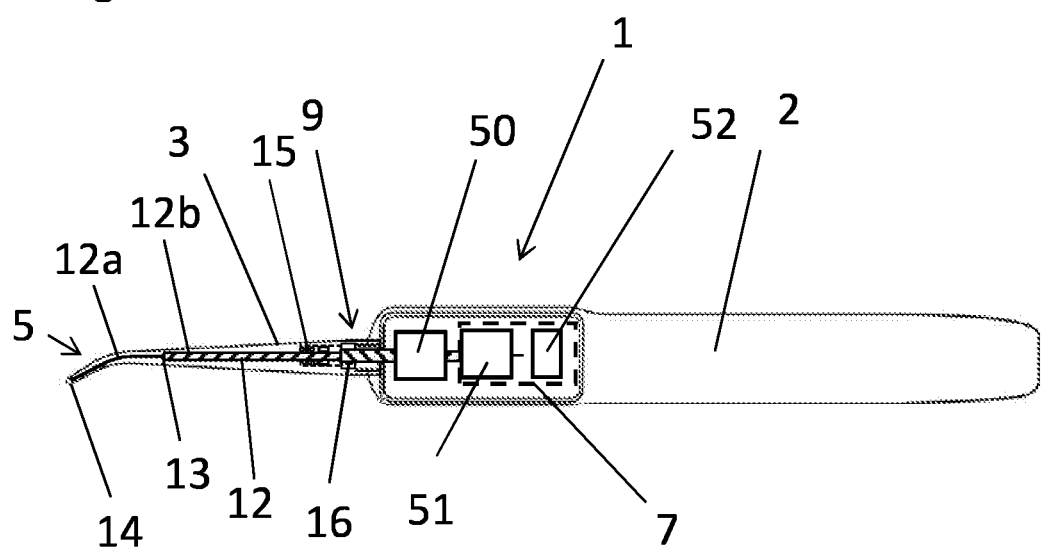
FIG. 12 shows an alternative embodiment of an operating device for the embodiment of FIGS. 10 and 11.

FIG. 12 shows an alternative embodiment of the surgical apparatus 1. This surgical apparatus 1 comprises a two-position mechanism 50 having a first position and a second position. In the first position a needle-end may be held by the first holding device 5, while the other needle-end may freely move into and out of the second holding device 6. In the second position a needle-end may be held by the second holding device 6, while the other needle-end may freely move into and out of the first holding device 5. The two-position switch mechanism 50 is thus configured to mechanically actuate both the first holding device 5 and the second holding device 6.

Only a single actuator 51 is required to move the two-position switch mechanism between the first position and the second position on the basis of an electrical switch signal provided by an operating switch 52. The actuator 51 and the operating switch 52 are arranged in the main body 2.

The invention claimed is:

1. A surgical suture apparatus for passing a double-ended surgical needle forwards and backwards, the surgical apparatus comprising:
   a first jaw element, comprising a first needle holder, wherein the first needle holder is arranged to hold a first needle-end of the surgical needle,
   a second jaw element comprising a second needle holder, wherein the second needle holder is arranged to hold a second needle-end of the surgical needle,
   a main body, wherein the first jaw element or a part thereof and the second jaw element or a part thereof are detachably mountable on the main body,
   a needle holder operating device, wherein the needle holder operating device is arranged to operate the first needle holder and the second needle holder to alternately hold the first needle-end by the first needle holder and the second needle-end by the second needle holder,
   wherein the first jaw element or the detachable part thereof and the second jaw element or the detachable part thereof, when mounted on the main body, are movable with respect to each other between a take-over position, wherein the surgical needle can be passed between the first needle holder and the second needle holder, and an open position, wherein the first needle holder and second needle holder are spaced further from each other, and
   a jaw element holder which releasably holds the first jaw element or the detachable part thereof and the second jaw element or the detachable part thereof in a fixed position with respect to the jaw element holder to facilitate coupling of the first jaw element or the detachable part thereof and the second jaw element or the detachable part thereof to the main body,
   wherein after coupling of the first jaw element or the detachable part thereof and the second jaw element or the detachable part thereof to the main body, the first jaw element or the detachable part thereof and the second jaw element or the detachable part thereof are configured to be released from the jaw element holder.

2. The surgical apparatus of claim 1, wherein the surgical apparatus comprises a first coupler configured to detachably couple the first jaw element or the detachable part thereof to the main body.

3. The surgical apparatus of claim 2, wherein the coupler comprises a coupling extension mounted on the main body or on the first jaw element and a coupling recess in the first jaw element or in the main body, respectively, and
   wherein the coupling recess is configured to receive the coupling extension in a coupling engagement.

4. The surgical apparatus of claim 3, wherein the coupling recess and the coupling extension are configured to couple with a snap-fit connection.

5. The surgical apparatus of claim 1, wherein the main body comprises the needle holder operating device.

6. The surgical apparatus of claim 1, wherein the first jaw element comprises a detachable jaw element part and a non-detachable jaw element part, and wherein the detachable jaw element part is detachably mounted on the non-detachable jaw element part.

7. The surgical apparatus of claim 1, wherein the needle holder operating device comprises:
- an operating switch to provide, upon activation of the operating switch, a switch signal, in particular an electrical switch signal, and
- at least one actuator configured to be controlled by the switch signal to operate the first needle holder and the second needle holder,
- wherein the operating switch and the at least one actuator are provided in the main body.

8. The surgical apparatus of claim 7, wherein the operating switch is configured to be automatically activated when the first and second jaw element are moved into the take-over position and/or wherein the surgical apparatus comprises an operating element configured to operate the operating switch.

9. The surgical apparatus of claim 7, wherein the at least one actuator comprises a first actuator to operate the first needle holder and a second actuator to operate the second needle holder.

10. The surgical apparatus of claim 7, wherein the surgical apparatus comprises a two-position mechanism having a first position in which a needle-end may be held by the first needle holder, and a second position in which a needle-end may be held by the second needle holder, wherein the at least one actuator is configured to actuate the two-position mechanism.

* * * * *